(12) United States Patent
Ringgenberg et al.

(10) Patent No.: US 7,191,672 B2
(45) Date of Patent: Mar. 20, 2007

(54) SINGLE PHASE SAMPLING APPARATUS AND METHOD

(75) Inventors: Paul D. Ringgenberg, Frisco, TX (US); Gregory N. Gilbert, Sugar Land, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 172 days.

(21) Appl. No.: 10/648,977

(22) Filed: Aug. 27, 2003

(65) Prior Publication Data

US 2004/0055400 A1    Mar. 25, 2004

Related U.S. Application Data

(60) Provisional application No. 60/406,619, filed on Aug. 27, 2002.

(51) Int. Cl.
*G01N 1/00* (2006.01)
(52) U.S. Cl. .................. 73/864.61; 73/152.23
(58) Field of Classification Search ............. 73/152.23, 73/152.24, 152.25, 152.26, 152.02, 864.62, 73/864.61; 175/59; 166/264
See application file for complete search history.

(56) References Cited

U.S. PATENT DOCUMENTS

| | | | |
|---|---|---|---|
| 5,337,822 A | 8/1994 | Massie et al. | 166/264 |
| 5,672,819 A | 9/1997 | Chin et al. | 73/152.41 |
| 5,741,962 A | 4/1998 | Birchak et al. | 73/152.16 |
| 5,934,374 A | 8/1999 | Hrametz et al. | 166/264 |
| 6,065,355 A | 5/2000 | Schultz | 73/864 |
| 2002/0060067 A1 | 5/2002 | Bolze et al. | 166/264 |
| 2003/0066646 A1 | 4/2003 | Shammai et al. | 166/264 |

FOREIGN PATENT DOCUMENTS

GB    2396648    6/2004

OTHER PUBLICATIONS

Great Britain Examination Report dated Jun. 21, 2005.
PCT International Search Report dated Dec. 5, 2003.

*Primary Examiner*—Robert Raevis
(74) *Attorney, Agent, or Firm*—Jones Day

(57) ABSTRACT

A single phase sampling apparatus and method for retrieving a formation fluid sample at or above the bubble point of the sample. The apparatus utilizes a gas charge contained between a sample piston and a charging piston to maintain a formation sample at the desired pressure. The charging piston utilizes the hydrostatic pressure present at the depth of the desired formation sample to compress and therefore increase the gas charge to the appropriate pressure necessary to maintain the formation sample at the desired pressure. The utilization of hydrostatic pressure to increase the pressure of the gas charge allows the use of a low pressure gas charging system to prepare the apparatus prior to sampling, thereby increasing the safety and ease of use of the device.

25 Claims, 4 Drawing Sheets

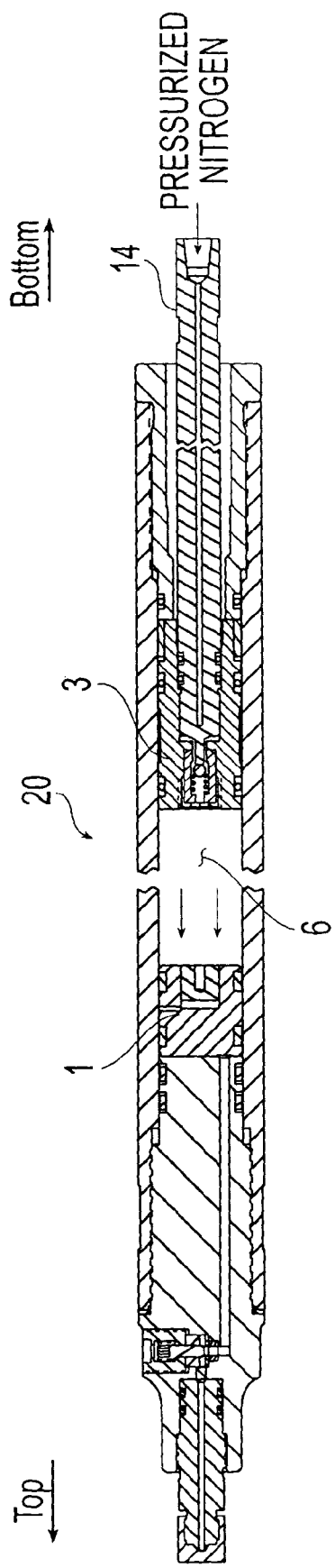
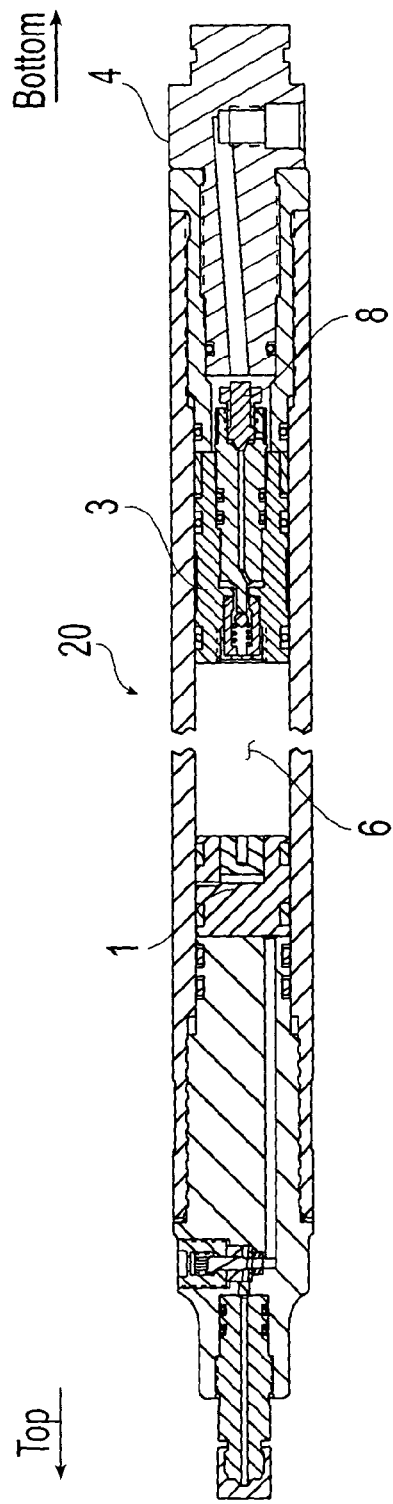
Fig. 4
Fig. 5

SINGLE PHASE SAMPLING APPARATUS AND METHOD

This application claims the benefit of U.S. Provisional Application 60/406,619, filed Aug. 27, 2002.

FIELD OF THE INVENTION

This invention relates generally to formation fluid testing and collection apparatus and more particularly to a single phase collection apparatus for a formation evaluation tool that collects formation fluids at a predetermined pressure and maintains the collected fluid pressure at such pressure throughout the sampling operation.

BACKGROUND OF THE INVENTION

In the oil and gas industry, a drilling fluid ("mud") is used during drilling of a wellbore to facilitate the drilling process and to maintain a hydrostatic pressure in the wellbore greater than the pressure in the formations surrounding the wellbore. This drilling fluid penetrates into or invades the formations for varying radial depths (referred to generally as the invaded zones) depending upon the types of the formation and drilling fluid used. Wireline formation testing tools lowered into the mud of the wellbore are used to monitor formation pressures, collect formation fluid samples from the wellbore and to predict performance of reservoirs around the wellbore. These formation evaluation tools typically contain an elongated body having an elastomeric packer that is sealingly urged against the zone of interest in the wellbore. Fluid is collected and brought to the surface for analysis to determine the properties of the fluids and the conditions of the zones or formations from where the fluids have been collected. During this process, it is critical that only uncontaminated fluids are collected, and in the same condition in which they exist in the formation.

Formation evaluation tools typically collect formation fluid by transferring such fluids from a probe into a sample chamber. Prior art formation evaluation tools such as sequential formation testers and repeat formation testers used large collection chambers that varied in size from one to five gallons to collect samples. Samples were not pumped into the chamber, but were forced into the chamber by the hydrostatic pressure of the formation acting against the atmospheric pressure in the chamber. The problem with these chambers was that once opened at the formation zone, they would ingest not only the sample, but also surrounding mud, rocks and other contaminates. Current formation testing tools overcome this problem by first testing fluids from the desired formations or zones of interest to ensure that the fluid is substantially free of mud filtrates, and then collecting fluids by pumping formation fluid into one or more sample bottles associated with the tool.

Because of the great difference in pressure between the formation (hydrostatic) and the interior of the sample bottle (atmospheric), there is a possibility that the formation fluid pumped into the chamber will vaporize, or "flash," due to a great decrease in pressure. In order to prevent or reduce the chances of the liquid vaporizing from a decrease in pressure, formation fluid is pumped into the chamber at a relatively slow rate. In addition, the tools are often equipped with restrictions to slow down the fluid flow rate into the chamber. Water cushions are also utilized to fill the chambers more uniformly. However, it is common for the collected single phase fluid to separate into a two phase sample containing vaporized gas. If the sample fluid pressure is reduced prior to arrival in the analysis lab, a lengthy procedure is required to recombine the sample back into a single phase as it was in situ. Additionally, asphaltenes are commonly present in the hydrocarbons and if the pressure in the chamber remains at a relatively low pressure, such asphaltenes tend to flocculate to form gel-type masses in the fluid. The flocculation process is substantially irreversible. Thus, it is desirable to withdraw and maintain the sample fluid at a pressure above the bubble point to maintain it in a single phase.

Additionally, the temperature difference between the surface elevation and the formation elevation can exceed several hundred degrees Fahrenheit. As the tool is retrieved, the chamber temperature drops, causing the pressure in the chamber to drop. This substantial pressure drop in the chamber can result in the pressure of the formation sample dropping below the bubble point, resulting in a multi-phase sample.

Attempts have been made to maintain the fluid sample in a single phase by applying a pressurized nitrogen charge against a sample piston located in the chamber. This forces the sample piston against the fluid sample to maintain its pressure at a sufficient level to prevent a phase change upon retrieval. However, this system is complex and requires the use of nitrogen at a pressure of over 20,000 psi. The danger and inconvenience of working with nitrogen at this extremely high pressure discourages its use.

The present invention addresses the above noted problems and provides a single phase collection apparatus in which collected formation fluid is maintained at a predetermined pressure above the bubble point to maintain the sample in a single phase. No water cushions are required to uniformly fill the chambers. The tool also automatically maintains the chamber pressure above the bubble point pressure during the entire sampling operation regardless of the change in the temperature surrounding the chamber.

SUMMARY OF THE INVENTION

The single phase collection apparatus of the present invention is therefore designed to maintain wellbore formation samples at a pressure above the bubble point as the sample is removed from the wellbore and is transported to a laboratory for analysis. By utilizing a nitrogen gas charge that acts against a sample piston, the sample is maintained at a pressure above the bubble point of the sample, thereby preventing the sample from separating into two phases. However, the nitrogen pressure utilized in this collection apparatus is significantly lower than the pressure used in existing single phase collection designs, and is therefore safer and easier to use. The amount of pressure present in a commercial nitrogen bottle generally will be sufficient to pre-charge the apparatus, without the need for nitrogen gas boosters to achieve the high pressures required.

The present invention modifies an existing Department of Transportation ("DOT") exempt sample bottle, simplifying DOT approval. Utilization of sample bottles that can be shipped as freight improves sample quality because the sample does not need to be transferred for transport. The use of these currently available sample bottles also allows in-the-field modification of existing DOT sample bottles. No additional leak paths for the sample are introduced by the modification, unlike older Drill Stem Test single phase samplers that created multiple leak paths with sliding seals and port crossing seals that affected the reliability of the devices. In addition, unlike the older designs which were limited to sample sizes of around 400 to 500 cubic centimeters due to the complexity of the mechanism, the simplified new design allows for the acquisition of larger sample sizes that may be more than twice that of existing designs. This is because the new design does not have any valves to shift, fluid to port or any other items to complicate and use up formation sample space. In addition, the size of the sample can be changed as desired because the nitrogen pressure can be adjusted for each sampling operation. A higher initial pressure is used to retrieve a smaller sample.

BRIEF DESCRIPTION OF THE DRAWINGS

FIG. 4 illustrates pressurized nitrogen gas being forced into the nitrogen gas chamber.
FIG. 5 illustrates a sample bottle prepared for use.

DETAILED DESCRIPTION OF THE INVENTION

The Single Phase Sample Collection Apparatus utilizes an existing sample bottle modified to allow for the introduction of pressurized nitrogen gas that acts against a sample piston of the device to maintain the sample at or above the bubble point of the sample. The collection apparatus utilizes the hydrostatic pressure present at the depth of the desired formation sample to compress the nitrogen gas "pre-charge" to the pressure of the formation sample, then maintains that pressure as the collection apparatus is removed from the wellbore.

Figure 1:
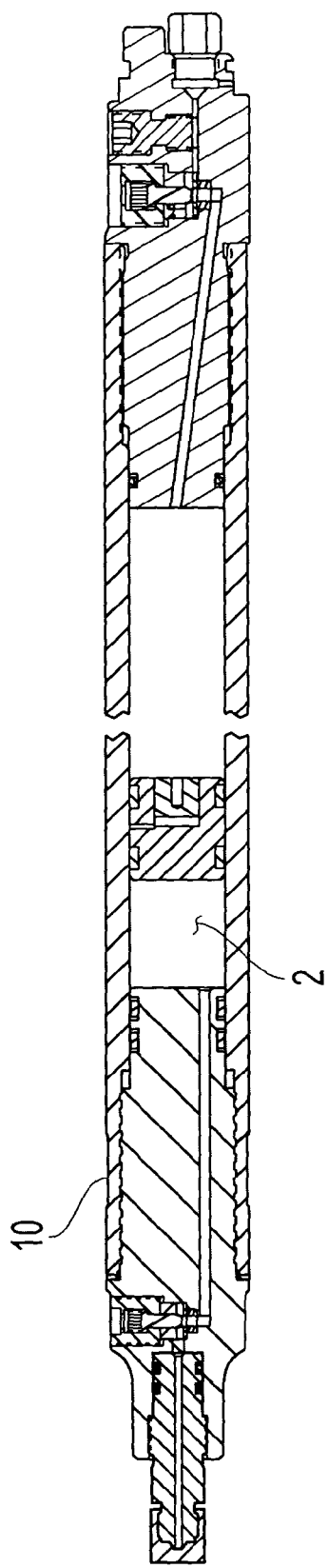
FIG. 1 illustrates a standard sample bottle.

FIG. 1 illustrates an existing formation evaluation tool sample bottle 10 designed to contain a formation sample located in a collection chamber 2. When at the desired formation depth, the formation sample is pumped into the collection chamber 2, pushing the sample piston 1 downwards until it comes into contact with an end cap located at the bottom of the sample bottle 10.

Figure 2:
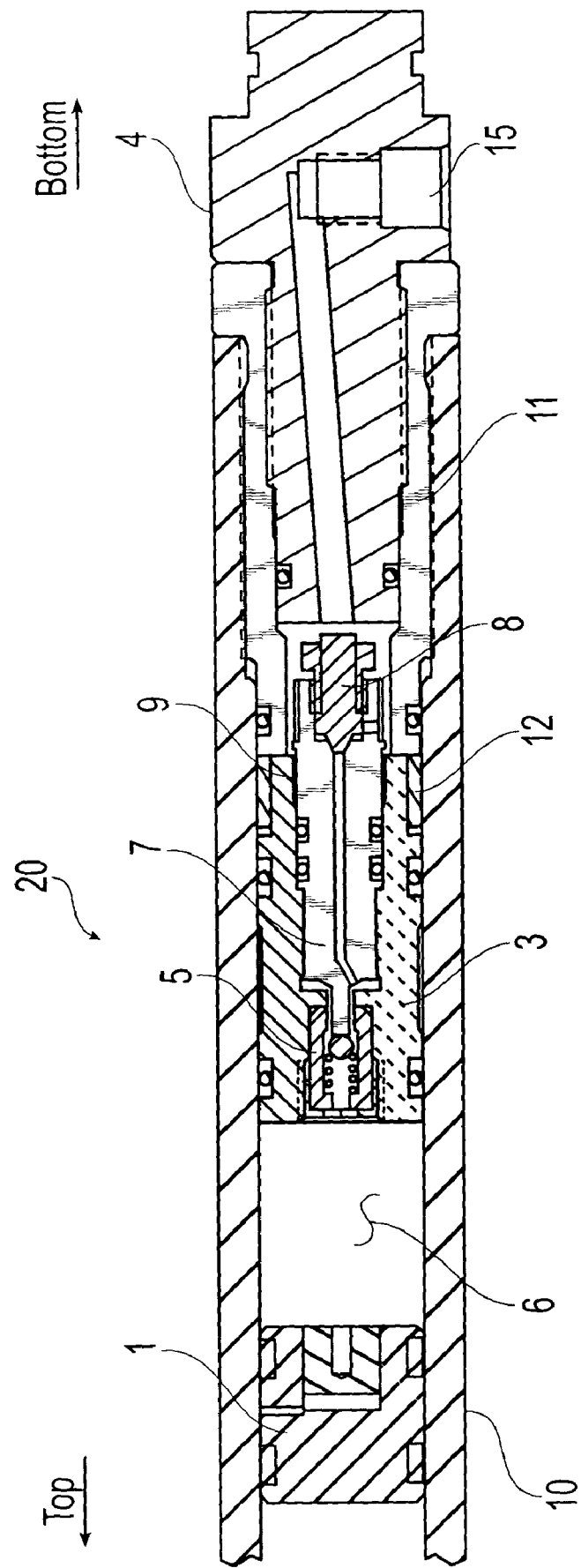
FIG. 2 illustrates the lower portion of a standard sample bottle modified according to the present disclosure.

The present invention single phase collection apparatus 20, as shown in FIG. 2, utilizes a current version sample bottle 10, but it is equipped with a nitrogen charging piston 3 inserted into the bore of the sample bottle 10. The sample bottle 10 is preferably a standard sample bottle that can be shipped as freight. The use of a sample bottle that can be shipped as freight improves sample quality because the sample does not need to be transferred to a separate shipping bottle for transport. The nitrogen charging piston 3 is positioned between the sample piston 1 and an end cap 4. The addition of the nitrogen charging piston 3 into the sample bottle 10 creates a variable size nitrogen gas chamber 6 between the nitrogen charging piston 3 and the sample piston 1.

The sample piston 1 is preferably made of an alloy steel, but can also be constructed from stainless steel, corrosion resistant alloy metals or other material with the appropriate properties to withstand the temperatures, pressures and corrosive conditions associated with such a device.

The nitrogen charging piston 3 is preferably made of an alloy steel, but can also be constructed from stainless steel, corrosion resistant alloy metals or other material with the appropriate properties to withstand the temperatures, pressures and corrosive conditions associated with such a device. The nitrogen charging piston 3 is sized to fit precisely within the bore of sample bottle 10. Gases are prevented from escaping around the nitrogen charging piston 3 by the use of one or more O-ring seals fitted into grooves inscribed into the outside diameter of the piston. An anti-extrusion backup seal may be placed on the low pressure side of the seal to help improve the seal. The nitrogen charging piston 3 has an open axial bore 9 allowing for the communication of gas through the piston. A check valve 5 is located within the axial bore 9 of the nitrogen charging piston and controls gas communication through the piston, into and out of the nitrogen gas chamber 6. Check valve 5 could also be a different type of valve such as a manually operated open/closed valve. A plunger 7, with a narrowed diameter section, fits into nitrogen charging piston 3. The plunger 7 is preferably threaded to allow engagement with matching threads on the inside diameter of the axial bore 9. When the plunger 7 is fully inserted into the piston 3, the narrowed diameter section of the plunger 7 functions to open check valve 5. The plunger 7 has an axial bore running through it with a removable release plug 8 to close off the end of the axial bore. O-ring seals at the outside diameter of the plunger 7 prevent gases from escaping around the plunger.

A case adaptor 11 with anti-rotation lugs 12, fits into and locks into the end of the sample bottle 10, and engages nitrogen charging piston 3 when the piston is pushed up to the end of its stroke. When engaged, the anti-rotation lugs 12 prevent the nitrogen charging piston 3 from rotating with respect to the lower case adaptor 11 so that the plunger 7 may be rotated for insertion/removal. The end cap 4 is inserted into and engages the case adaptor 11. The end cap 4 comprises a port 15 that is open to hydrostatic pressure when the collector apparatus is inserted into a wellbore, thereby exposing the nitrogen charging piston 3 to hydrostatic pressure.

Figure 3:
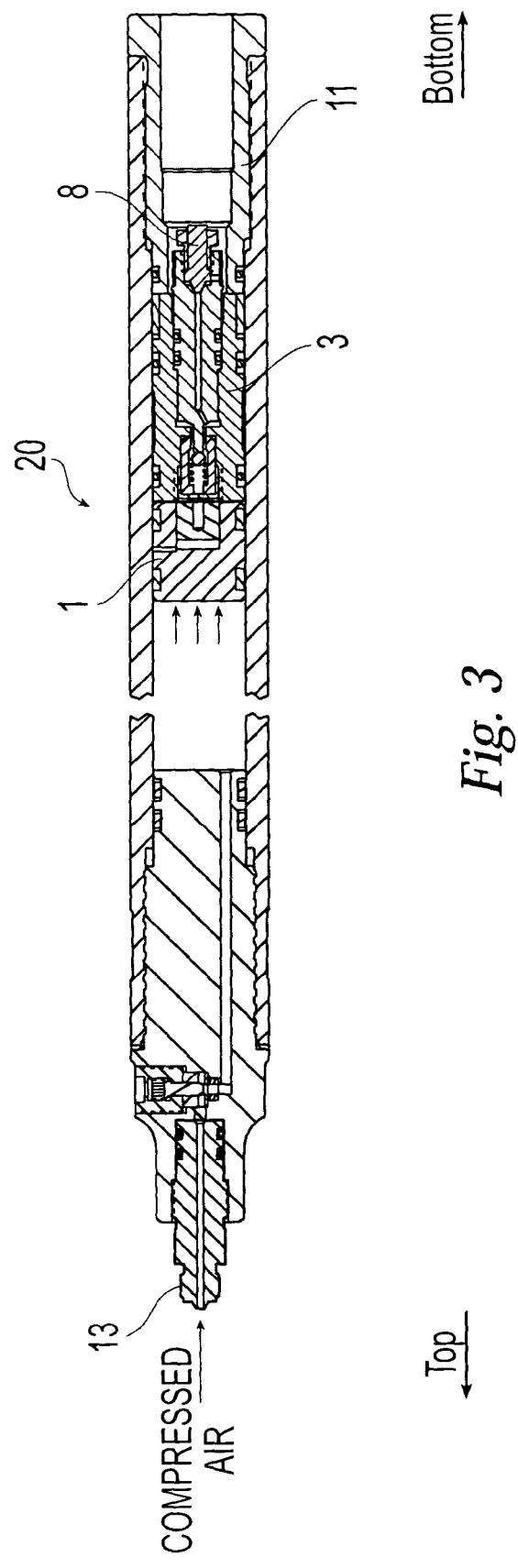
FIG. 3 illustrates the sample piston and nitrogen charging piston being forced to the bottom of the bottle.

In order to collect a formation sample, the single phase collection apparatus 20 is assembled as shown in FIG. 2. As shown in FIG. 3, the end cap 4 is removed and an air pressure source is connected to the sub 13. Air pressure at approximately 100 psi is then introduced into the collection apparatus, forcing the sample piston 1 and the nitrogen charging piston 3 down towards the case adaptor 11. The nitrogen charging piston 3 stops when it reaches the case adaptor 11, and the anti-rotation lugs 12 engage the nitrogen charging piston 3 thereby preventing rotation with respect to the case adaptor 11. Release plug 8 is then removed to allow any trapped gases between the sample piston 1 and the nitrogen charging piston 3 to escape, thereby minimizing the volume between sample piston 1 and the nitrogen charging piston 3.

The plunger 7 is then removed from the nitrogen charging piston 3 and a purge adapter 14, connected to a pressurized nitrogen supply, is inserted into the nitrogen charging piston 3, opening the check valve 5, as shown in FIG. 4. The air pressure source attached to the sub 13 is removed and nitrogen gas is forced through the purge adaptor 14, through the check valve 5, and into the nitrogen gas chamber 6. As nitrogen gas fills the nitrogen gas chamber 6, the sample piston 1 is forced upwards until nitrogen gas fills nearly the entire volume of the sampler. Although nitrogen gas is the preferred pressurizing medium, it is conceivable that other pressurizing gases could be utilized to achieve the same function. However, nitrogen has the advantages of easy availability and has well known physical properties. Once this pre-charging pressure reaches the proper level, preferably around 3,000 psi, the purge adapter 14 is removed, thereby closing off check valve 5. The release plug 8 is then reinstalled in the plunger 7, and then the plunger 7 is reinstalled into the nitrogen charging piston 3. The narrowed diameter section of the plunger 7 opens check valve 5, allowing nitrogen gas to act against the O-rings of the plunger 7. This prevents the formation of any regions in the apparatus with only atmospheric pressure, which would increase the differential pressure acting on the seal. The end cap 4 is then replaced, as shown in FIG. 5.

Figure 6:
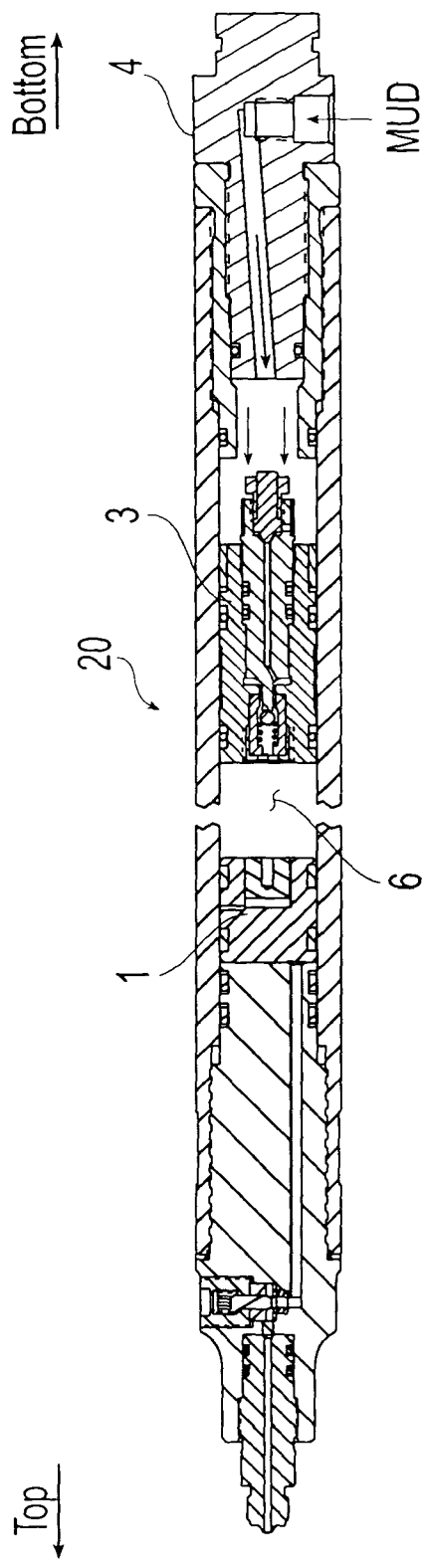
FIG. 6 illustrates hydrostatic pressure forcing the nitrogen charging piston upwards.

Once assembled and pre-charged, one or more of the single phase collection apparatus 20 is inserted into the multi-chamber section ("MCS") of a formation evaluation tool to collect formation samples. As the tool is lowered down into the wellbore, the open port 15 of the end cap 4 is exposed to mud at hydrostatic pressure and the nitrogen charging piston 3 is forced upwards once hydrostatic pressure is greater than the initial nitrogen gas pressure, compressing the nitrogen gas within the nitrogen gas chamber 6 so that the pressure of the nitrogen gas equals the hydrostatic pressure, as in FIG. 6.

Figure 7:
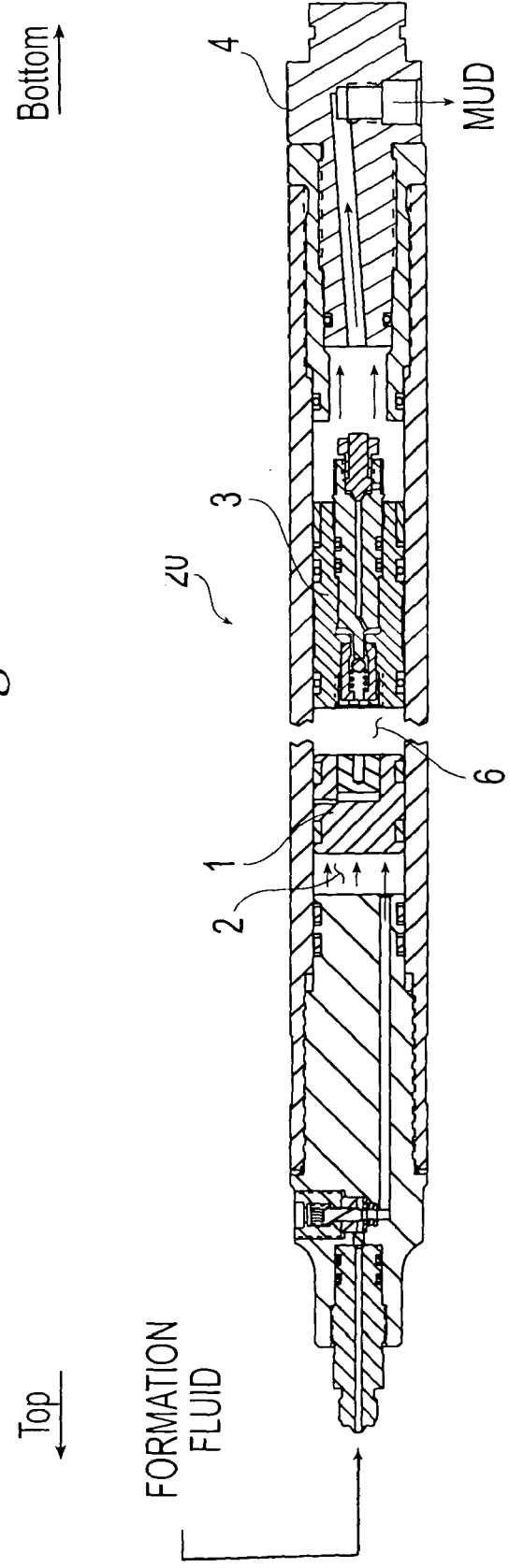
FIG. 7 illustrates formation fluid being pumped into the sample chamber.

When a sample is to be taken, the appropiate valve of the MCS is opened and the desired formation fluid is pumped into the collection chamber 2, thereby forcing both the sample piston 1 and the nitrogen charging piston 3 downward towards the case adaptor 11 as shown in FIG. 7. Mud is forced out of the open port 15 of the end cap 4 as both the sample piston 1 and the nitrogen charging piston 3 move downwards. Once the nitrogen charging piston 3 engages the case adaptor 11, the pressure of both the sample and the nitrogen gas increases as pumping continues. Once the desired overpressure has been attained, the MCS valve is closed trapping the sample and the nitrogen gas at a pressure above hydrostatic.

As the collection apparatus 20 is retrieved from the wellbore, the formation sample shrinks as the sample cools. However, the highly compressible nitrogen gas acting against the sample piston 1 maintains the pressure of the sample above the bubble point.

At the surface, a shipping end cap replaces the end cap 4 for transportation and storage. If cool temperatures are expected during shipping, additional fluid can be pumped in through the shipping end cap to compress the nitrogen further, thereby helping to maintain the sample at a high pressure.

The removal of the sample from the collection apparatus 20 is accomplished using conventional techniques to remove formation samples from a sample bottle. Thus, fluid is pumped in to the collection apparatus 20 to force the sample out of the collection chamber 2.

What is claimed is:

1. A formation fluid sample bottle comprising:
    a cylindrical tube with an enclosed top end and an open bottom end;
    a sample piston slidingly inserted into said cylindrical tube to form a sample chamber inside said cylindrical tube between said enclosed top end and said sample piston;
    a charging piston slidingly inserted into said cylindrical tube between said sample piston and said open bottom end to form a pressurized gas chamber inside said cylindrical tube between said sample piston and said charging piston; and
    an end cap fixed to said open bottom end;

wherein:
    said charging piston includes a valve to allow the introduction of a pressurizing gas into said pressurized gas chamber.

2. The formation fluid sample bottle of claim 1, wherein said enclosed top end includes an opening with a valve to allow a formation fluid sample to be introduced into said sample chamber.

3. The formation fluid sample bottle of claim 2, wherein said end cap includes an open port.

4. The formation fluid sample bottle of claim 3, wherein said charging piston has an outer circumference and additionally comprises:
    at least one O-ring located at said outer circumference;
    an axial bore extending through said charging piston; and
    a check valve positioned in said axial bore.

5. The formation fluid sample bottle of claim 4, wherein said charging piston additionally comprises a plunger inserted into said axial bore.

6. The formation fluid sample bottle of claim 5, wherein said plunger additionally comprises:
    a distal end and a proximal end;
    an axial bore;
    a narrowed diameter section at said distal end; and
    a release plug inserted into said axial bore at said proximal end.

7. The formation fluid sample bottle of claim 6, wherein:
    said plunger additionally has an outer circumference and further comprises:
    at least one O-ring located at said outer circumference; and
    said outer circumference of said plunger is provided with threads for attachment to said axial bore of said charging piston.

8. The formation fluid sample bottle of claim 7, additionally comprising pressurized nitrogen gas inserted into said pressurized gas chamber.

9. The formation fluid sample bottle of claim 8, wherein said charging piston is formed from material selected from the group consisting of alloy steel, stainless steel and corrosion resistant alloy metal.

10. A single phase formation evaluation tool comprising:
    at least one formation fluid sample bottle with an enclosed top end, an open bottom end and an axial bore extending through said formation fluid sample bottle;
    a sample piston slidingly inserted into said axial bore of said formation fluid sample bottle to form a collection chamber within said axial bore, between said enclosed top end and said sample piston;
    a charging piston slidingly inserted into said axial bore of said formation fluid sample bottle below said sample piston, to form a pressurized gas chamber within said axial bore, between said sample piston and said charging piston; and
    an end cap fixed to said open bottom end of said formation fluid sample bottle.

11. The single phase formation evaluation tool of claim 10, wherein said charging piston has an outer circumference and additionally comprises:
    at least one O-ring located at said circumference;
    an axial bore extending through said charging piston; and
    a check valve positioned in said axial bore.

12. The single phase formation evaluation tool of claim 11, wherein said charging piston additionally comprises a plunger inserted into said axial bore.

13. The single phase formation evaluation tool of claim 12, wherein said plunger additionally comprises:
   a distal end and a proximal end;
   an axial bore;
   a narrowed diameter section at said distal end; and
   a release plug inserted into said axial bore at said proximal end.

14. The single phase formation evaluation tool of claim 13, wherein:
   said plunger additionally has an outer circumference and further comprises:
   at least one O-ring located at said outer circumference; and
   said outer circumference of said plunger is provided with threads for attachment to said axial bore of said piston.

15. The single phase formation evaluation tool of claim 14, additionally comprising pressurized nitrogen gas inserted into said pressurized gas chamber.

16. The single phase formation evaluation tool of claim 15, wherein said charging piston is formed from material selected from the group consisting of alloy steel, stainless steel and corrosion resistant alloy metal.

17. The single phase formation evaluation tool of claim 10, additionally comprising:
   a case adaptor positioned at said open bottom end of said formation fluid sample bottle; and
   wherein said end cap is fixed to said case adapter.

18. The single phase formation evaluation tool of claim 17, additionally comprising anti-rotation lugs mounted on said case adaptor to engage said charging piston.

19. The single phase formation evaluation tool of claim 10, wherein said charging piston includes a check valve to introduce pressurized gas into said pressurized gas chamber.

20. A pressurizing piston for use in collecting formation fluid samples downhole and maintaining the pressure of the sample above the bubble point of the sample, comprising:
   a cylindrical main body with a distal end, a proximal end and a threaded axial bore;
   a check valve inserted into said axial bore at said distal end of said main body;
   a plunger with a narrowed diameter distal section, an open proximal end, an axial bore, an outer circumference with at least one O-ring located at said outer circumference, and threads located on said outer circumference engaged to said cylindrical main body threaded axial bore; and
   a release plug inserted into said plunger open proximal end to seal off said plunger axial bore.

21. A method for downhole fluid sample collection comprising the steps of:
   providing a tube with a first end and a second end, and a first piston and a second piston located within said tube;
   inserting pressurized gas in the space between said first and second piston;
   lowering the tube downhole;
   collecting a formation fluid sample in the space between the first end of the tube and said first piston, wherein collecting a formation fluid sample comprises allowing downhole hydrostatic pressure to force said second piston toward said first piston to further pressurize said pressurized gas;
   raising said tube with said formation fluid sample.

22. A method as in claim 21, wherein the step of inserting comprises forcing pressurized gas through said second piston into said pressurized gas chamber.

23. A method as in claim 21 further comprising the step of inserting said tube into a formation evaluation tool.

24. A method as in claim 21, wherein the step of collecting a formation fluid sample comprises pumping formation fluid between the enclosed top end of the tube and said first piston.

25. A method as in claim 21, wherein the inserted pressurized gas is nitrogen.

* * * * *